United States Patent [19]

Schiff et al.

[11] Patent Number: 5,661,556
[45] Date of Patent: Aug. 26, 1997

[54] SYSTEM FOR MEASURING THE TOTAL INTEGRATED SCATTER OF A SURFACE

[75] Inventors: Tod F. Schiff, Beaverton; Marvin L. Bernt, Scappoose, both of Oreg.

[73] Assignee: Schmitt Measurement Systems, Inc., Portland, Oreg.

[21] Appl. No.: 618,977

[22] Filed: Mar. 20, 1996

Related U.S. Application Data

[63] Continuation of Ser. No. 562,876, Nov. 27, 1995.

[60] Provisional application No. 60/003,220 Sep. 5, 1995.

[51] Int. Cl.$^6$ ............................................. G01J 1/04
[52] U.S. Cl. ............................................. 356/236; 250/228
[58] Field of Search ............................ 356/236, 371, 356/445, 446; 250/228; 359/387

[56] References Cited

U.S. PATENT DOCUMENTS

| | | | |
|---|---|---|---|
| 3,648,056 | 3/1972 | Buttweiler et al. | 250/228 |
| 4,150,898 | 4/1979 | Suga | 356/236 |
| 4,743,759 | 5/1988 | Boutet | 250/228 |
| 4,746,214 | 5/1988 | Akiyama et al. | 356/236 |
| 4,873,430 | 10/1989 | Juliana et al. | 250/228 |
| 4,972,092 | 11/1990 | Schmitt et al. | 356/236 |
| 5,369,481 | 11/1994 | Berg et al. | 356/236 |
| 5,517,315 | 5/1996 | Snail et al. | 356/236 |

FOREIGN PATENT DOCUMENTS

1921432  11/1970  Germany ............................ 356/236

*Primary Examiner*—Hao Q. Pham
*Attorney, Agent, or Firm*—Madson & Metcalf

[57] ABSTRACT

A system and method for characterizing a surface are disclosed. The system includes a light source and source optics which direct a beam of light toward the surface. A first optical integrating device is positioned and configured to receive a first portion of the scattered light which corresponds to a first range of spatial frequencies. A second optical integrating device is positioned and configured to receive a second portion of the scattered light corresponding to a second range of spatial frequencies. In one embodiment, an integrating sphere is employed as the first optical integrating device. The sphere includes a sampling aperture which is surrounded by a light absorption region on the interior of the sphere. Total integrated scatter data is generated for each range of spatial frequencies and is used to approximate the spectral scatter function of the surface. RMS roughness is then approximated for any range of spatial frequencies.

12 Claims, 4 Drawing Sheets

SYSTEM FOR MEASURING THE TOTAL INTEGRATED SCATTER OF A SURFACE

RELATED U.S. APPLICATION

This application is a continuation of application Ser. No. 08/562,876, filed Nov. 27, 1995, which is a continuation in part of U.S. provisional application Ser. No. 60/003,220, filed Sept. 5, 1995.

BACKGROUND

1. The Field of the Invention

The present invention is related to optical methods and apparatus for the non-contact inspection and characterization of a surface. More particularly, the present invention is related to methods and apparatus for approximating the "spectral integrated scatter" function of a surface, thereby permitting the total integrated scatter of the surface over any desired spatial frequency limits to be determined.

2. Technical Background

The ability to accurately measure physical properties of a surface is important in a variety of applications. Such physical properties include roughness, texture, waviness, and information relating to the profile of the surface. The measure of such physical properties is generally referred to as "characterizing" a surface.

For example, in the field of computer hardware, it is preferable that computer hard disks be manufactured with a known roughness, generally referred to as "texture" by that industry. As a quality control measure, hard disk manufacturers desire a measurement device which would permit them to quickly and easily measure surface roughness as precisely as possible. Current technology trends are moving toward surface texture levels requiring surface measurement down to about the 10 Angstrom level. It would be preferable if surface roughness could be measured to within 1 Angstrom or less.

Other applications where precise roughness measurements are desirable include the computer chip wafer industry. In manufacturing chip wafers, it is desirable that the front surface of the wafer be as smooth as possible and that the back side of the wafer is finished to a known roughness.

Also, the optical industry, particularly mirror manufacturers, desires high-precision measurement devices to gauge the quality of the surfaces of their optics. Such optics are typically employed in imaging systems such as those utilized in telescopes and satellites.

Some surface characterization instruments operate by contacting the surface. A profilometer is an example of such a device. A profilometer operates by dragging a stylus across a surface. The stylus is physically connected to a recorder which traces the profile of the surface. Mathematical analysis of the profile may be conducted to determine physical properties of the surface.

For many applications, such contact-based instruments and methods are unacceptable because of the risk of contamination or other damage to the surface. Additionally, they are extremely slow and do not provide sufficient resolution to be effective for use in many applications. Thus, there exists a great need for noncontact surface characterization devices and methods.

Surface inspection devices based on optics have generally proved to be the most effective at noncontact surface characterization. Such optical devices typically operate by directing a beam of light at the surface and measuring the amount and direction of nonspecular light scattered off the surface. Through the analysis of such data, much information regarding the character of the surface can be ascertained.

One such noncontact, optical-based device is the scatterometer. To measure roughness, for example, the scatterometer measures the scatter intensity of the scattered light at every scatter angle in a selected plane. This information can then be used to generate the "power spectral density" function for that plane. The power spectral density function illustrates the distribution of the power scattered by each spatial frequency. The roughness of the surface can then be approximated by integrating the power spectral density function.

One disadvantage to the use of such scatterometers is that because the scatterometer measures only one plane of the scatter hemisphere, only a small portion of the total information about the surface is obtained. If the surface is isotropic, such methods are generally accurate. For isotropic surfaces, the total roughness is determined by performing three-dimensional integration on the power spectral density function. However, if the surface is nonisotropic, such as surfaces having a "lay" to them or randomly rough surfaces, a scatterometer may produce grossly inaccurate results.

One method for characterizing nonisotropic surfaces is to measure the scatter intensity at every point in the scatter hemisphere. The sample data can then be manually integrated to determine the roughness. Such a method can be performed with an "out-of-plane" scatterometer. This method is extremely time consuming and is therefore not practical for most applications which require rapid inspection and analysis.

In an attempt to make scatter measurement more efficient and versatile, it has been noted that plotting the power spectral density versus the spatial frequency on a log-log plot will generally result in a straight-line curve. Thus, by obtaining two representative points on this line, the curve can be approximated. By integrating this function over selected spatial frequency limits, surface roughness can be determined.

One difficulty with this process is that the power spectral density data is two dimensional; thus, the process only works well for isotropic surfaces. Additionally, because of the limitations on the physical size of the detector, the representative points used to generate the curve are close together. Hence, any noise in the data could substantially decrease the accuracy of the fit of the curve.

Measuring additional data points to improve the fit of the curve becomes difficult because of the complexity of the necessary instrumentation. Additionally, the math to include additional data points becomes unduly complicated. Also, the inclusion of more data points still does not account for nonisotropic variations in the surface. Thus, attempting to add additional data points to improve the curve fit is not viable for many applications.

The prior art method which is currently preferred for characterizing nonisotropic surfaces is the "total integrated scatter" method. According to this generally accepted method, an optical integrating device, such as a hollow sphere, generally referred to as an "integrating sphere," is placed over the surface of the sample. The integrating sphere has an input aperture through which a beam of light may be directed into the device. A sampling aperture on the other end of the sphere permits the light to be directed onto the surface and allows light scattered off the surface to enter the sphere. An output aperture is also configured into the sphere for permitting the reflected specular beam to exit the sphere.

Thus, the light scattered off the surface remains within the sphere and its intensity can be measured with a detector. Advantageously, this method measures all of the scattered light regardless of variations in the surface.

Because the integrating sphere captures all of the scattered light, it performs a physical integration of the power spectral density function. Because the integration is performed directly by the sphere, some specific information about the power spectral density function is not obtained. For example, information regarding the slope of the function is not obtained.

Additionally, when using an integrating sphere, the limits of integration are set by the physical configuration of the sphere and cannot be changed without changing the physical configuration of the sphere. Also, because of physical limitations on the size and configuration of the sphere and on how the sphere may be positioned with respect to the sample, some limits of integration may not be obtainable.

Other problems associated with integrating spheres include the difficulty of preventing stray light from entering the sphere while containing all of the scattered light within the sphere. A principal source of stray light is the optics in the light source. Although the source optics focus the main beam, the optics also act as a scatter source.

By reducing the size of the input aperture of the sphere, much stray light can be blocked from entering the sphere. If, however, the size of the input aperture is too small, it will clip the main beam and cause diffraction of the main beam into the sphere, thereby introducing more stray light into the sphere. Thus, the input aperture must be sized larger than the main beam, thereby allowing some stray light to enter the sphere.

Another method of reducing stray light within the sphere is to increase the distance between the source optics and the input aperture. This decreases the effective size of the input aperture from the perspective of the source optics. Of course, making the instrument too large is not desirable. Thus, there are physical and practical limitations on the extent to which the distance between the source optics and the input aperture can be maximized.

The size of the output aperture also, affects the amount of stray light contained within the sphere. The stray light introduced by the source optics is concentrated in the region surrounding the main beam. Thus, by increasing the size of the output aperture, much of this stray light will exit the sphere and therefore not be measured. However, much of the light Scattered off the surface is also concentrated around the area of the main beam. Hence, increasing the size of the output aperture permits more scattered light to exit the sphere, thereby decreasing sensitivity of the instrument.

Additionally, the range of spatial frequencies over which the sphere integrates is determined in part by the size of the output aperture. If the size of the output aperture can be kept to a minimum, the range of spatial frequencies over which the sphere may integrate is increased.

For some applications, it is necessary to compare data obtained from different integrating devices. Because integrating devices frequently operate over different limits of integration (i.e., over different spatial frequency ranges), meaningful comparison of data obtained from different integrating devices is often impossible.

From the foregoing, it will be appreciated that it would be an advancement in the art to provide improved noncontact methods and apparatus for characterizing a surface. Indeed, it would be an advancement if such methods and apparatus could produce accurate results for nonisotropic surfaces.

It would be a further advancement in, the art to provide an improved integrating sphere which would be small, convenient to use, and which could accomplish rapid inspection and analysis. It would also be an advancement in the art if such an integrating sphere could minimize stray light while maximizing the amount of scattered light measured by the sphere.

It would be a substantial improvement in the art if such an integrating sphere could be used to obtain the total integrated scatter for a surface over any desired spatial frequency limits, thereby permitting a variety of physical properties of the surface to be characterized and allowing comparison with data obtained from other integrating spheres.

Such methods and apparatus are disclosed and claimed herein.

BRIEF SUMMARY AND OBJECTS OF THE INVENTION

The present invention is directed to novel apparatus and methods for approximating the total integrated scatter of a surface. In accordance with one method of the present invention, a plurality of bands of spatial frequencies is selected with each band having an upper and a lower limit. This is preferably done by selecting two bands of spatial frequencies with the first band having an upper limit ($f_1$) and a lower limit ($f_2$) and the second band having an upper limit ($f_3$) and a lower limit ($f_4$). In one preferred method, $f_1$, $f_2$, $f_3$, and $f_4$ are selected such that the following relationship is satisfied:

$$\frac{f_3}{f_4} = \frac{f_1}{f_2}.$$

Preferably, $f_2$ and $f_3$ are selected such that $f_2$ equals $f_3$.

A beam of light having a known wavelength is directed onto the surface at a known incident angle with respect to the surface. The total scatter of light corresponding to each of the selected bands of spatial frequencies is then collected. This is preferably accomplished by using optical integrating devices, such as integrating spheres, lenses, or mirrors.

The total integrated scatter of each of the selected bands of spatial frequencies is measured by detecting the intensity of the collected light. The total integrated scatter data and the upper and lower limits of spatial frequency for each of the selected bands are used to approximate the "spectral integrated scatter" function, a three-dimensional function representative of the integrated power spectral density function. With the spectral integrated scatter function known, the total integrated scatter of the surface over any set of spatial frequency limits may be determined.

In accordance with an alternative method of the present invention, the information derived from the method described above is utilized to characterize the surface. With the total integrated scatter determined for any set of desired spatial frequency limits, physical properties of the surface may be characterized. Such physical properties include RMS roughness, sometimes referred to as texture, waviness, representative profile, or haze.

In accordance with this alternative method, the RMS roughness ($\sigma$) of the surface may be ascertained for a surface having a roughness less than the wavelength of the beam of light ($\lambda$) by solving the following equation:

$$\sigma_{\it eff} = \frac{\lambda}{4\Pi\cos\theta_i} \sqrt{TIS_{\it eff}},$$

where TIS is the total integrated scatter over desired spatial frequency limits and $\theta_i$ is the incident angle of the beam of light with respect to the normal of the surface.

In accordance with one preferred method, the beam of light is directed onto the surface at an incident angle ($\theta_i$) less than about 10 degrees with respect to the normal of the surface. The RMS roughness ($\sigma$) for a surface whose roughness is less than the wavelength of the beam of light ($\lambda$) may then be determined according to the following equation:

$$\sigma = \frac{\lambda}{4\Pi} \sqrt{TIS}.$$

One preferred apparatus for practicing the present invention includes a system for characterizing a surface by approximating the spectral integrated scatter function of the surface over the entire range of spatial frequencies. This system includes a light source capable of producing a beam of light at a predetermined wavelength ($\lambda$). In a presently preferred system, the light source generates a laser beam.

Positioned adjacent the light source are source optics for directing the beam of light toward the surface at an incident angle ($\theta_i$) with respect to the normal of the surface. The beam of light may then reflect off the surface to thereby create a reflected specular beam and scattered light.

A first optical integrating device is positioned and configured to receive a first portion of the scattered light while permitting a second portion of scatter light to pass through. The first optical integrating device may be a sphere, a mirror, a lens, or other optical integrating device modified in accordance with the teachings of the present invention. In a presently preferred embodiment, the first optical integrating device is a hollow sphere.

The sphere is configured with an input aperture, a sampling aperture, and an output aperture. The light source, source optics, and sphere are positioned such that the beam of light may be directed through the input aperture, through the sampling aperture, and onto the surface, and such that the second portion of the scattered light and the specular beam are directed out of the sphere through the output aperture.

The first optical integrating device is configured such that the first portion of the scattered light received by the first optical integrating device extends from a first scatter angle ($\theta_1$) to a second scatter angle ($\theta_2$) and such that the second portion of the scattered light which passes through the first optical integrating device extends from a third scatter angle ($\Theta_3$) to a fourth scatter angle ($\theta_4$). It is presently preferred that the scatter angles ($\theta_n$) be selected to correspond to predetermined spatial frequencies ($\theta_n$) of the surface such that the following relationship is satisfied: $\theta_n = \sin^{-1}(\sin\theta_i - f_n\lambda)$. Thus, the scatter angles are measured from the direction of the reflected specular beam.

A second optical integrating device is positioned and configured to receive the second portion of the scattered light. Additionally, the second optical integrating device is configured to permit the specular beam to pass through the second optical integrating device. Like the first optical integrating device, the second optical integrating device may include an integrating sphere, a mirror, a lens, or other devices capable of suitable configuration. The second optical integrating device preferably comprises a focusing mirror configured with an output aperture through which the specular beam may pass.

The source optics are configured such that the specular beam is positioned within the output aperture of the focusing mirror. Preferably, however, the source optics focus the specular beam at the output aperture of the focusing mirror.

The apparatus of the present invention also includes a first detector positioned to detect the intensity of the first portion of the scattered light. In the preferred embodiment in which an integrating sphere is employed, the detector is mounted in the wall of the sphere.

A second detector is positioned to detect the intensity of the second portion of the scattered light. In the preferred embodiment, the focusing mirror is positioned to receive and reflect the second portion of the scattered light into the second detector. Finally, a specular detector is positioned to detect the intensity of the specular beam after it passes through the second optical integrating device.

Typical prior art integrating spheres employ a baffle to shield the detector from light scattered off the surface directly into the detector. Advantageously, the present invention eliminates the need for such a baffle by positioning the first detector within the integrating sphere such that the angle ($\theta_D$) between the normal of the surface and the line between the sampling aperture and the first detector is greater than $\theta_1$.

In accordance with one presently preferred embodiment of the invention, the input aperture of the hollow sphere has a circular perimeter with a radius ($r_i$), the sampling aperture of the hollow sphere has a circular perimeter with a radius ($r_s$), the output aperture of the hollow sphere has a circular perimeter with a radius ($r_0$), the focusing mirror has a circular perimeter with a radius ($r_{2O}$), and the output aperture of the focusing mirror has a circular perimeter with a radius ($r_{2i}$).

In a preferred embodiment, the system of the present invention is configured so that the incident angle of the beam of light ($\theta_i$) is less than about 10 degrees, the first scatter angle ($\theta_1$) is greater than about 45 degrees, the second scatter angle ($\theta_2$) and the third scatter angle ($\theta3$) are equal and are less than about 20 degrees, and the fourth scatter angle ($\theta_4$) is also less than about 20 degrees.

The radius of the perimeter of the sampling aperture ($r_s$) is determined as a function of the first scatter angle ($\theta_1$), thereby defining one of the limits of the first band of spatial frequencies. The radius of the perimeter of the output aperture of the hollow sphere ($r_0$) is similarly determined as a function of the second scatter angle ($\theta_2$), thereby defining the other limit of the first band of spatial frequencies.

The output aperture of the mirror should be sized as small as possible while allowing the entire specular beam to pass through the mirror. The mirror should be configured to receive the scattered light corresponding to the second band of spatial frequencies. For a system designed such that $f_2$ is equal to $f_3$ (i.e., $\theta_2=\theta_3$), the focusing mirror must be sized large enough to capture all of the light reflected off the surface which passes through the output aperture of the sphere.

It has been found that the performance of the system of the present invention can be substantially increased by configuring the interior surface of the first optical integrating device with an absorption region surrounding the sampling aperture. This absorption region is preferably formed by coating the region with black glass or another coating which absorbs light at the wavelength of the light source. The remaining portion of the interior surface of the sphere which is outside the absorption region comprises a reflective region, such as those which are common to integrating spheres. Importantly, the reflectance of the absorption region is less than the reflectance of the reflective region at the wavelength of the light source.

It is presently preferred that the absorption region of the interior surface of the sphere has a circular perimeter and is positioned concentric with the sampling aperture. The focusing mirror and the second detector are preferably positioned such that the outside diameter of the absorption region is imaged at the maximum field of view of the second detector.

In such a system, it is preferred that the source optics be positioned to direct the incident beam at the surface at an incident angle ($\theta_i$) which is less than about 10 degrees. Also, it is presently preferred to configure the system such that the second scatter angle ($\theta_2$) is equal to the third scatter angle ($\theta_3$) and is less than about 20 degrees and such that the fourth scatter angle ($\theta_4$) is less than about 20 degrees.

In accordance with a further aspect of the present invention, an improved device for measuring the total integrated scatter of a surface is disclosed. The device is used to measure total integrated scatter between two spatial frequencies. Thus, it may be used alone, as is commonly known in the art of integrating spheres, or it may be used in combination with other integrating devices in accordance with the teachings of other aspects of the present invention.

The device includes a light source capable of producing a beam of light at a known wavelength range. Preferably the light source is a laser source producing light at a known wavelength ($\lambda$). Source optics are provided for directing the incident beam of light toward the surface at an incident angle $\theta_i$. The device is configured to measure scattered light between a first scatter angle ($\theta_1$) and a second scatter angle ($\theta_2$), where the scatter angles are related to spatial frequencies by $\theta_n = \sin^{-1}(\sin\theta_1 - f_n\lambda)$.

The device further includes a hollow sphere which is configured with an input aperture, a sampling aperture, and an output aperture. Each of these apertures is configured with a circular perimeter. The light source, source optics, and sphere are positioned relative to each other such that the incident beam may be directed through the input aperture, through the sampling aperture, and onto the surface and such that the specular beam reflected off the surface is directed out of the sphere through the output aperture. A detector is positioned within the sphere to detect the intensity of scattered light within the sphere. A specular detector is positioned outside the sphere such that it can detect the intensity of the reflected specular beam.

As with embodiments of the present invention disclosed above, the hollow sphere is an optical integrating device having an interior surface which includes an absorption region surrounding the sampling aperture. The absorption region is preferably formed by coating the region with black glass or other coating which absorbs light at the wavelength of the light source. The remaining portion of the interior surface of the sphere which is outside the absorption region comprises a reflective region. Importantly, the reflectance of the absorption region is less than the reflectance of the reflective region at the wavelength of the light source.

The source optics are preferably configured to focus the specular beam at the output aperture of the hollow sphere, thereby reducing the amount of stray light and enabling the sizes of all apertures to be kept to a minimum.

The absorption region is preferably configured with a circular perimeter and is sized such that stray light generated by the source optics which enters the sphere through the input aperture will be imaged on the absorption region. The output aperture should be sized to permit all stray light which is specularly reflected off the surface to exit the sphere. Thus, virtually none of the stray light entering the sphere will be detected by the scatter detector. It will either be absorbed by the absorption region or exit the sphere through the output aperture.

Finally, in this embodiment of the present invention, the baffle to shield the scatter detector may be eliminated by positioning the scatter detector within the integrating sphere such that the angle ($\theta_D$) between the specular beam and the line between the sampling aperture and the detector is greater than $\theta_1$.

Thus, it is an object of the present invention to provide improved methods and apparatus for the noncontact characterization of surfaces.

These and other objects and advantages of the present invention will become more fully apparent by examination of the following description of the preferred embodiments and the accompanying drawings.

BRIEF DESCRIPTION OF THE DRAWINGS

A more particular description of the invention briefly described above will be rendered by reference to the appended drawings. Understanding that these drawings only provide information concerning typical embodiments of the invention and are not therefore to be considered limiting of its scope, the invention will be described and explained with additional specificity and detail through the use of the accompanying drawings, in which.

DETAILED DESCRIPTION OF THE PREFERRED EMBODIMENTS

The present invention is directed to novel apparatus and methods for use in measuring the total integrated scatter of a surface. In accordance with one method of the present invention, the total integrated scatter of a surface is approximated for any set of spatial frequency limits. This is accomplished by determining the three-dimensional power spectral density function, referred to herein as the "spectral integrated scatter" function. Because the three-dimensional power spectral density function is representative of the entire hemisphere of scatter off a surface, it provides information for isotropic and nonisotropic surfaces whose roughness is less than the wavelength of light used to characterize the surface. With the three-dimensional power spectral density function known, the total integrated scatter over any set of spatial frequency limits can readily be determined. This method may be used to compare data from other integrating devices which operate over different spatial frequency limits.

The three-dimensional power spectral density function is determined by selecting a plurality of bands of spatial frequencies. In a presently preferred method, only two bands of spatial frequencies are selected because with data from two bands, the three-dimensional power spectral density function can be accurately determined. The first band is defined by an upper limit ($f_1$) and a lower limit ($f_2$). Similarly, the second band is defined by an upper limit ($f_3$) and a lower limit ($f_4$).

A beam of light having a known wavelength ($\lambda$) is directed onto the surface at a known incident angle ($\theta_i$) with respect to the normal of the surface. The total scatter of light, or "total integrated scatter," corresponding to each of the selected bands of spatial frequencies is then collected. This is preferably accomplished by using optical integrating devices, such as integrating spheres, lenses, or mirrors.

The boundaries of the bands of spatial frequencies are determined by the physical configuration of the apparatus utilized in collecting the scatter. Preferably, the bands are selected and the apparatus correspondingly configured such that the following relationship is satisfied:

$$\frac{f_3}{f_4} = \frac{f_1}{f_2},$$

and such that $f_2$ equals $f_3$. Additionally, it is presently preferred that $f_1$ be maximized and $f_4$ be minimized, thereby making the boundaries as wide as possible. For small incident angles, such as incident angles less than about 10 degrees, the maximum theoretical value of $f_1$ is approximately equal to $(\sin\theta_i)/\lambda$, where $\lambda$ is the wavelength of the incident beam of light. Hence, it is desirable that $f_1$ be as close as possible to this theoretical limit.

The total integrated scatter of each of the selected bands of spatial frequencies is measured by collecting scattered light with the integrating devices over a range of scatter angles ($\theta_n$) which corresponds to the spatial frequency band. It is presently preferred that the scatter angles ($\theta_n$) be selected to correspond to predetermined spatial frequencies ($f_n$) of the surface such that the following relationship is satisfied: $\theta_n = \sin^{-1}(\sin\theta_i - f_n\lambda)$. Thus, by calculating the scatter angles which correspond to the limits of the spatial frequency band sought to be measured, a system may be configured to collect the scattered light over that range of scatter angles. The total integrated scatter over the selected range of scatter angles may then be measured. The total integrated scatter data and the upper and lower limits of spatial frequency for each of the selected bands are used to determine the spectral integrated scatter (SIS) function.

Figure 1:
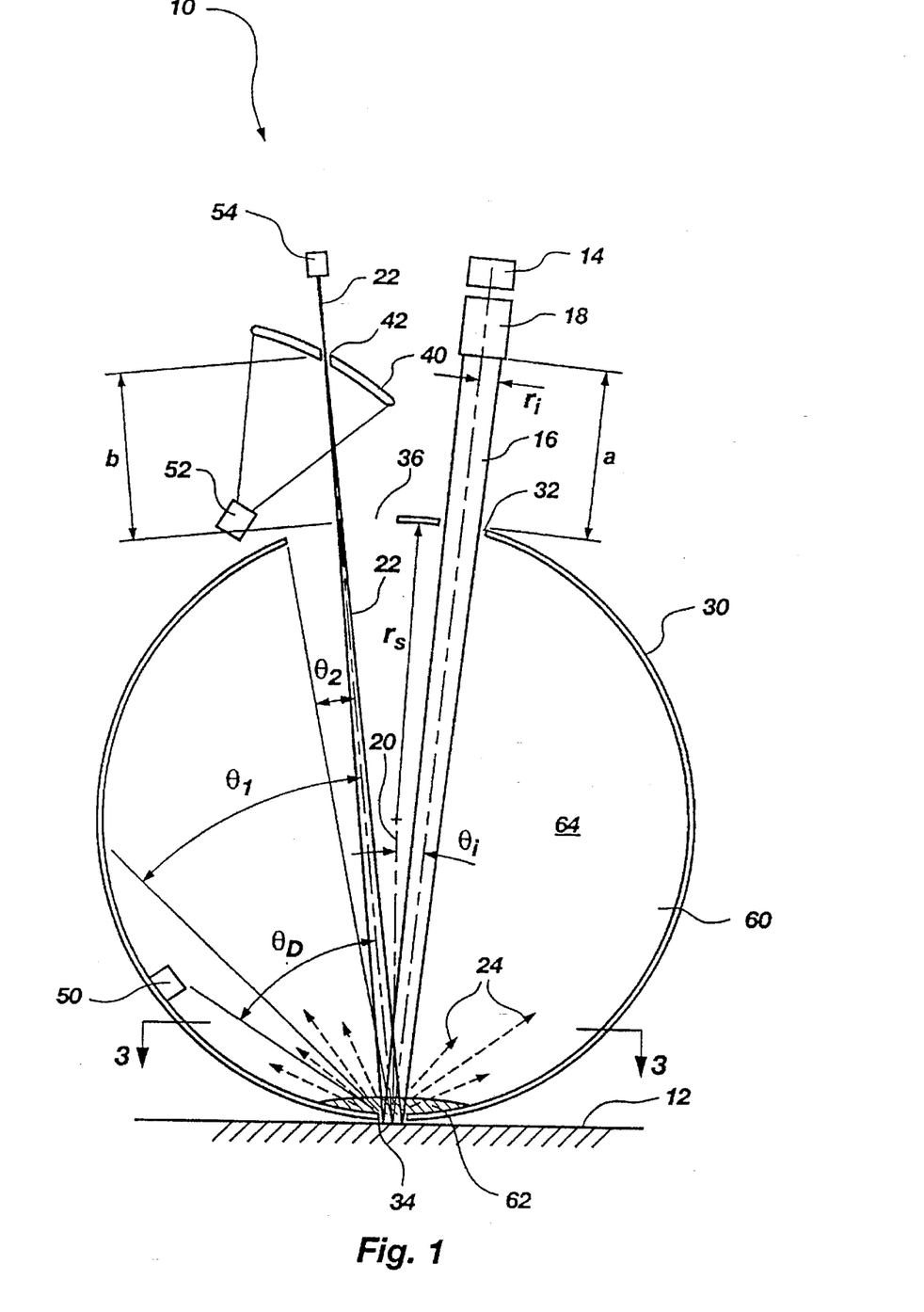
FIG. 1 is a schematic view of one preferred embodiment of an apparatus of the present invention with the integrating sphere illustrated in cross section.

As illustrated in FIG. 1, one embodiment of a surface characterization system built according to the teachings of the present invention is generally designated at 10. The system 10 includes a light source capable of producing a beam of light at a predetermined wavelength ($\lambda$). In the illustrated embodiment of the system 10, the light source is a laser source 14 which generates a laser beam 16 having a wavelength of 0.670 microns. One such laser source is the model "TOLD9215" laser diode marketed by Toshiba.

Positioned adjacent the laser source 14 are source optics 18 for directing the beam of light 16 toward the surface at an incident angle ($\theta_i$) with respect to the normal 20 of the surface 12. In this embodiment, the laser and source optics produce an incident beam having a circular cross section. The source optics may include any of those conventional optical configurations known to one of skill in the art. When the beam of light 16 hits the surface 12, a specular beam 22 and scattered light 24 are reflected off the surface.

The system 10 further includes a first optical integrating device which is positioned and configured to receive a first portion of the scattered light while permitting a second portion of scattered light to pass through. The first optical integrating device may be a sphere, a mirror, a lens, or any other optical integrating device modified in accordance with the teachings of the present invention. In this preferred embodiment, the first optical integrating device is a hollow sphere 30 having a radius ($R_s$).

Such hollow spheres, generally referred to as "integrating spheres," are common in the art of optical measurement systems. The interior surface of the sphere 30 is a reflective material having a reflectance greater than about 90 percent. One presently preferred integrating sphere 30 is that sold by Labsphere, Inc. of New Hampshire, U.S.A., as model "SRM-99" under the SPECTRALON trade name, in which the interior surface has a reflectance of about 99.1 percent.

The sphere 30 is configured with an input aperture 32, a sampling aperture 34, and an output aperture 36. The apertures 32, 34, and 36 each have a circular perimeter with radii $r_i$, $r_s$, and $r_o$, respectively. The apertures are positioned within the sphere 30 and the sphere is positioned relative to the light source 14 such that the beam of light 16 may be directed through the input aperture 32, through the sampling aperture 34, and onto the surface 12, and such that the second portion of the scattered light and the specular beam 22 are directed out of the sphere 30 through the output aperture 36.

The integrating sphere 30 is configured such that it captures the first portion of scattered light; that is, the scattered light extending from a first scatter angle ($\theta_1$) to a second scatter angle ($\theta_2$). The output aperture 36 is sized to permit the second portion of the scattered light, extending from a third scatter angle ($\theta_3$) to a fourth scatter angle ($\theta_4$), to exit the sphere 30. As illustrated in FIG. 1, the "scatter angle" is measured with respect to the specular beam 22.

The system 10 further includes a second optical integrating device which is positioned and configured to receive the second portion of the scattered light as it exits the sphere 30 through the output aperture 36. Like the first optical integrating device, the second optical integrating device may include an integrating sphere, a mirror, a lens, or other integrating device. In this embodiment, the second optical integrating device comprises a focusing mirror 40 configured with an output aperture 42 through which the specular beam 22 may pass. The mirror 40 and the aperture 42 in the mirror each have a circular perimeter with radii $r_{2o}$ and $r_{2i}$, respectively. The focusing mirror 40 is sized and positioned with respect to the sphere 30 such that it receives the scattered light extending from the third scatter angle ($\theta_3$) to the fourth scatter angle ($\theta_4$).

The source optics 18 are configured such that the specular beam 22 is positioned within the output aperture 42 of the focusing mirror 40. Preferably, however, the source optics 18 focus the specular beam 22 at the output aperture 42.

The system 10 also includes a first detector 50 positioned to detect the intensity of the first portion of the scattered light. In this embodiment, the detector 50 is mounted in the wall of the sphere 30. Conventional integrating spheres typically employ a baffle to shield the detector from light scattered off the surface directly into the detector. Advantageously, the present invention eliminates the need for such a baffle by positioning the first detector within the integrating sphere such that the angle ($\theta_D$) between the specular beam 22 and the line between the sampling aperture and the first detector is greater than ($\theta_1$).

A second detector 52 is positioned to detect the intensity of the second portion of the scattered light. The second detector 52 is positioned relative to the focusing mirror 40 such that the second portion of the scattered light is reflected into the second detector 52. Accordingly, the focusing mirror 40 is configured to focus the second portion of the scattered light within the field of view of the second detector 52.

Finally, a specular detector 54 is positioned to detect the intensity of the specular beam 22 after it passes through the second optical integrating device. The specular detector 54 must be positioned such that its field of view encompasses all of the specular beam 22. The specular detector 54 should be a "low scatter" detector to prevent it from being a source of stray light. The detectors 50, 52, and 54 may include any detector known for such a use, including commercially available silicon photo diodes.

A principal source of "secondary" stray light is the hardware and mounting apparatus associated with all portions of the system 10 outside the sphere 30. The generation of such secondary stray light can be substantially eliminated by ensuring that the exterior surfaces are made out of, or coated with, a material which is light absorbing at the wavelength of the incident beam 16.

For high angles of incidence ($\theta_i$) of the beam 16, the standoff distance of the sphere from the surface 12 and the geometry and alignment of the system must be carefully controlled. At high incident angles, a minor variation in the standoff distance of the sphere from the surface will result in a large change in the position of the reflected specular beam 22 with respect to the output aperture 36. If the change of position of the specular beam 22 is too great, it will no longer be aligned with the output aperture 36, thereby causing it to hit the interior of the sphere 30. Obviously, this would result in catastrophic failure of the system. Hence, to make the system as versatile as possible, it is preferred to keep the incident angle small.

It is, therefore, preferred that the system 10 be configured so that the incident angle ($\theta_i$) of the beam of light is less than about 10 degrees, the first scatter angle ($\theta_1$) is greater than about 45 degrees, the second scatter angle ($\theta_2$) and the third scatter angle ($\theta_3$) are equal and are less than about 20 degrees, and the fourth scatter angle ($\theta_4$) is also less than about 20 degrees. In one presently preferred embodiment, the incident angle ($\theta_i$) is about five degrees, the first scatter angle ($\theta_1$) is about 45 degrees, the second scatter angle ($\theta_2$) and the third scatter angle ($\theta_3$) are equal and are about six degrees, and the fourth scatter angle ($\theta_4$) is about one degree. These angles are merely representative of one presently preferred system 10. One of skill in the art will, of course, appreciate that a variety of physical configurations may be constructed without departing from the teachings of the present invention.

Physical limitations on the construction of the system 10 may restrict the selection of spatial frequencies (and their corresponding scatter angles) over which the system may operate. For example, care must be taken to ensure that hardware associated with the light source 14 and the source optics 18 does not interfere with the collection path of the mirror 40. Similarly, hardware associated with the mirror 40, the specular detector 54, and the second detector 52 must not interfere with the incident beam 16. Additionally, the input aperture 32 and the output aperture 36 should not physically intersect each other.

The radius of the perimeter of the sampling aperture ($r_s$) should be as large as possible to facilitate access to the surface 12. However, as the size of the sampling aperture is increased, the interior surface area of the sphere is correspondingly decreased. Decreasing the interior surface area of the sphere causes a deterioration in the light collection efficiency of the sphere.

Figure 2:
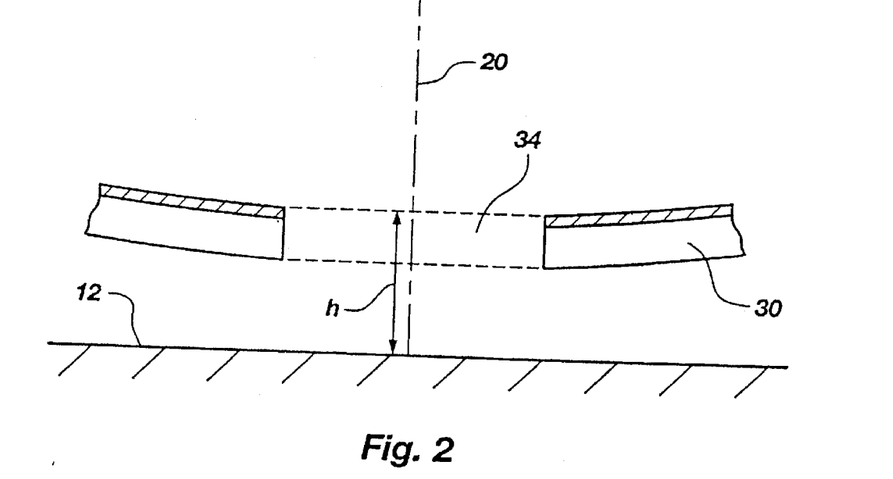
FIG. 2 is a cross-sectional view of a portion of the apparatus of FIG. 1.

The preferred radius ($r_s$) of the sampling aperture 34 is determined as a function of the first scatter angle ($\theta_1$). In the embodiment described herein, the radius of the perimeter of the sampling aperture ($r_s$) is approximately equal to h(tan$\theta_1$), where h is the distance from the surface 12 to the interior surface of the hollow sphere 30 at the sampling aperture along the line 20 normal to the surface 12 (FIG. 2). Thus, for a given first scatter angle or first spatial frequency, the preferred size of the sampling aperture can readily be determined.

The radius of the perimeter of the output aperture of the hollow sphere ($r_0$) is determined as a function of the second scatter angle ($\theta_2$). In this preferred system, the radius of the perimeter of the output aperture of the hollow sphere ($r_0$) is equal to $2R_s \tan\theta_2$.

In a system with the source optics 18 focusing the specular beam 22 at the output aperture 42 of the focusing mirror 40, the preferred radius of the perimeter of the input aperture 32 of the hollow sphere ($r_i$) is defined by the following relationship:

$$r_i = K \frac{4R_S}{4R_S + a + b} r_1,$$

for values of K≧1, where a is the distance along the beam of light 16 from the source optics 18 to the input aperture 32 of the hollow sphere 30 and b is the distance along the path of the specular beam 22 from the output aperture 36 of the hollow sphere 30 to the focusing mirror 40. Preferably, the system is configured such that a and b are equal. If the beam of light is a laser beam, K is chosen to be greater than or equal to $\sqrt{2.5}$.

For a system designed such that $f_2$ is equal to $f_3$, the focusing mirror 40 must be sized large enough to capture all of the light reflected off the surface 12 which passes through the output aperture 36 of the sphere 30. This is achieved by configuring the focusing mirror such that the minimum radius ($r_{2o}$) of its perimeter is about equal to $\tan\theta_3(b+2R_s)$. If the system is configured such that $\theta_2$ equals $\theta_3$, then the preferred minimum radius of the perimeter of the focusing mirror ($r_{2o}$) is defined by the following relationship:

$$r_{2o} = \left(1 + \frac{b}{2R_S}\right) r_0.$$

The output aperture of the mirror 40 should be sized as small as possible while allowing all of the specular beam 22 to pass through the mirror 40. The radius of the perimeter of the output aperture of the focusing mirror ($r_{2i}$) in this preferred embodiment is approximately equal to $(\tan\theta_4)(b+2R_s)$.

In the presently preferred system 10 in which the incident angle ($\theta_i$) is less than about 10 degrees and in which the second scatter angle ($\theta_2$) is equal to the third scatter angle ($\theta_3$) and is less than about 20 degrees, the radius of the perimeter of the output aperture of the focusing mirror ($r_{2i}$) may be defined by the following relationship:

$$r_{2i} = \left(1 + \frac{2R_S + b}{2R_S + a}\right) r_S + \left(\frac{2R_S + b}{2R_S + a}\right) r_1,$$

where $r_1$ is the radius of the cross section of the incident beam 16 at the source optics 18 and $r_s$ is the radius of the sampling aperture 34.

Figure 3:
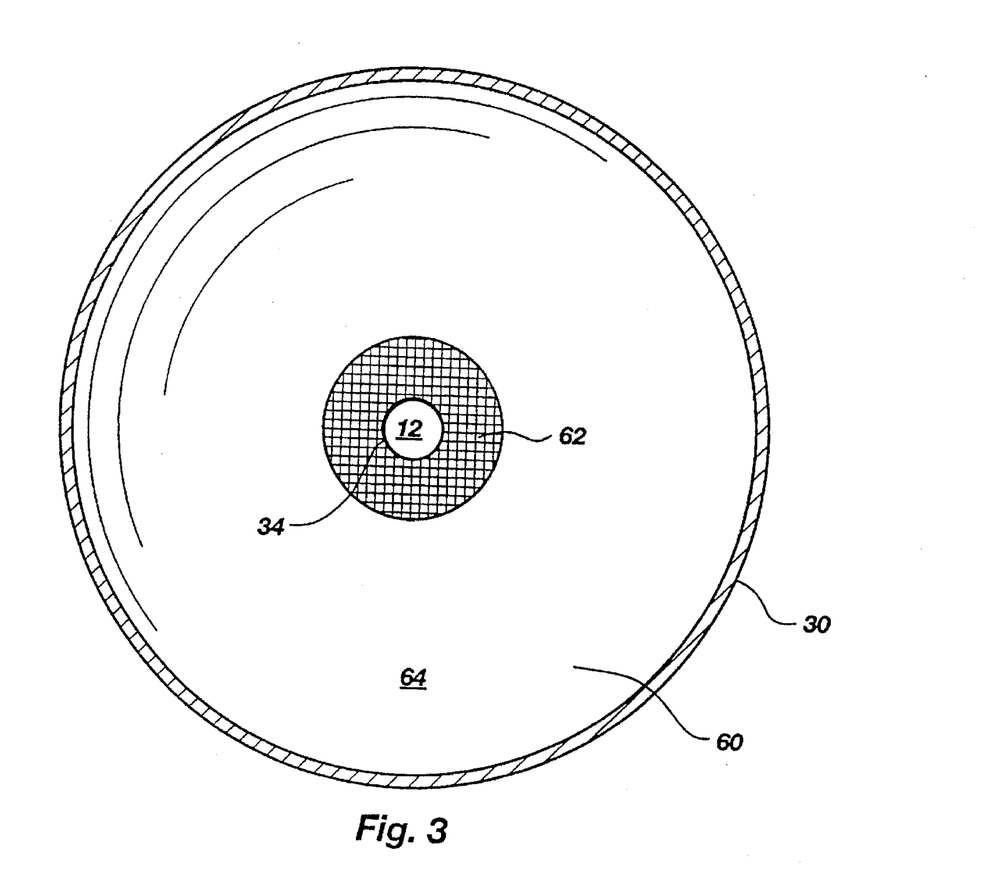
FIG. 3 is a cross-sectional view taken along line 3—3 of FIG. 1.

In accordance with another aspect 0f the present invention as illustrated in FIG. 3, the integrating sphere 30 has an interior surface 60 which includes an absorption region 62 surrounding the sampling aperture 34. The absorption region 62 is formed by coating the region with a coating which absorbs light at the wavelength of the light source ($\lambda$). One such presently preferred coating is magnesium fluoride, generally referred to as "black glass." Of course, one of skill in the art will appreciate that other light-absorbing materials or coatings may also be utilized.

That portion of the interior surface 60 of the sphere which lies outside the absorption region 62 comprises a reflective region 64. The reflective region is configured to reflect light at the wavelength of the light source and may comprise any of those reflective materials known to those of skill in the art of integrating spheres. Importantly, the materials utilized on the interior surface 60 are selected such that the reflectance of the absorption region 62 is less than the reflectance of the reflective region 64 at the wavelength of the light source.

The reflectance of the absorption region 62 will generally be less than about 10 percent with the reflectance of the reflective region 64 being greater than about 90 percent. It is preferred, however, that the reflectance of the absorption region 62 be less than about 5 percent and the reflectance of the reflective region 64 be greater than about 95 percent. In one presently preferred embodiment of the invention, the absorption region 62 has a reflectance of about 2 percent and the reflective region 64 has a reflectance of about 99.1 percent. One presently preferred material for use as the reflective region 64 is that sold under the SPECTRALON trade name by Labsphere, Inc. of New Hampshire, U.S.A. One presently preferred coating for use in forming the absorption region 132 is black glass.

The purpose of the absorption region is to absorb the stray light generated by the source optics 18 which enters the sphere. Thus, the absorption region 62 should be configured to cover that portion of the source optics 18 which is imaged on the interior surface of the sphere through the input aperture 32. The absorption region should be kept as closely as possible to this ideal size, as making it any larger will result in undue amounts of scattered light being absorbed.

The source optics 18 are centered on the input aperture 32 and are configured to produce a beam 16 with a circular cross section. Accordingly, the absorption region 62 of the interior surface 60 has a circular outside diameter and is positioned concentric with the sampling aperture 34. The focusing mirror 40 and the second detector 52 are preferably positioned such that the outside diameter of the absorption region 62 is imaged at the maximum field of view of the second detector 52, thereby minimizing the amount of stray light which may enter the second detector 52.

In one embodiment of the system 10 of the present invention including the absorption region in the integrating sphere, $\theta_1$, $\theta_2$, $\theta_3$, and $\theta_4$ are selected such that the following relationship is satisfied:

$$\frac{\sin\theta_3 - \sin\theta_i}{\sin\theta_4 - \sin\theta_i} = \frac{\sin\theta_1 - \sin\theta_i}{\sin\theta_2 - \sin\theta_i}.$$

Alternatively, the system may be configured such that $\theta_2$ equals $\theta_3$.

In operation, the system 10 of FIG. 1 may be utilized to characterize a surface, such as the surface 12, by measuring the total integrated scatter of the surface 12 over two bands of spatial frequencies, with the first band ranging from $f_1$ to $f_2$ and the second band ranging from $f_3$ to $f_4$. The system 10 is positioned a predetermined distance above a surface 12 and the light source 14 activated to direct the incident beam 16 onto the surface 12.

The light scattered off the surface between the first scatter angle ($\theta_1$) and the second scatter angle ($\theta_2$) is retained within the sphere 30 and its intensity is detected by the detector 50. Scattered light between the third scatter angle ($\theta_3$) and the fourth scatter angle ($\theta_4$) exits the sphere 30 through the output aperture 36 and is reflected off the mirror 40 and into the second detector 52 which measures its intensity. The reflected specular beam 22 also exits the sphere through the output aperture 36 and passes through the aperture 42 in the mirror 40 and enters the specular detector 54 which measures its intensity.

The signals from the detectors are processed in accordance with standard signal processing techniques well known in the art. They are amplified, filtered, and processed by an analog-to-digital converter before being processed by a microprocessor. One of skill in the art will readily appreciate how to process the signals to produce output data in a variety of useful forms.

The power detected by the detector 50 is the total integrated scatter over the first band of spatial frequencies, or $TIS_1$. Similarly, the power detected by the second detector 52 is the total integrated scatter over the second band of spatial frequencies, or $TIS_2$.

With TIS1 and TIS2 known, the spectral integrated scatter (SIS) function may now be approximated. This is accomplished by making the assumption that the SIS function is linear in log-log space. With this assumption, the SIS function is then determined by finding the slope of the SIS function when plotting spatial frequency versus total integrated scatter over each band on a log-log scale. The slope (n) of the SIS function is approximated as:

$$n = \frac{\ln\left(\frac{TIS_1}{TIS_2}\right)}{\ln(K)},$$

where $$K = \frac{f_3}{f_4} = \frac{f_1}{f_2}.$$

With the slope of the spectral integrated scatter function known, the total integrated scatter of the surface over any set of desired spatial frequency limits may be determined. This is generally done to facilitate comparison of data generated by another measurement system based on an integrating device, but being configured to measure over different spatial frequency limits.

Thus, the effective total integrated scatter ($TIS_{eff}$) of the surface 12 over a range of spatial frequencies from $f_{min}$ to $f_{max}$ which, for example, corresponds to the spatial frequency range measured by another instrument, is determined by the following equation:

$$TIS_{eff} = TIS_1 \left( \frac{f_{min}^n - f_{min}^n}{f_1^n - f_2^n} \right).$$

The effective RMS roughness ($\sigma_{eff}$) can then be determined according to the standard RMS roughness equation:

$$\sigma_{eff} = \frac{\lambda}{4\pi\cos\theta_i} \sqrt{TIS_{eff}}.$$

When the incedent angle($\theta_i$) is less than about 10 degrees with respect to the normal of the surface, the equation for determining RMS roughness may be reduced to:

$$\sigma_{eff} = \frac{\lambda}{4\pi} \sqrt{TIS_{eff}}.$$

By calculating the effective roughness, the roughness of a surface measured with the system of the present invention can be easily compared to the roughness of a surface measured with a different system.

Figure 4:
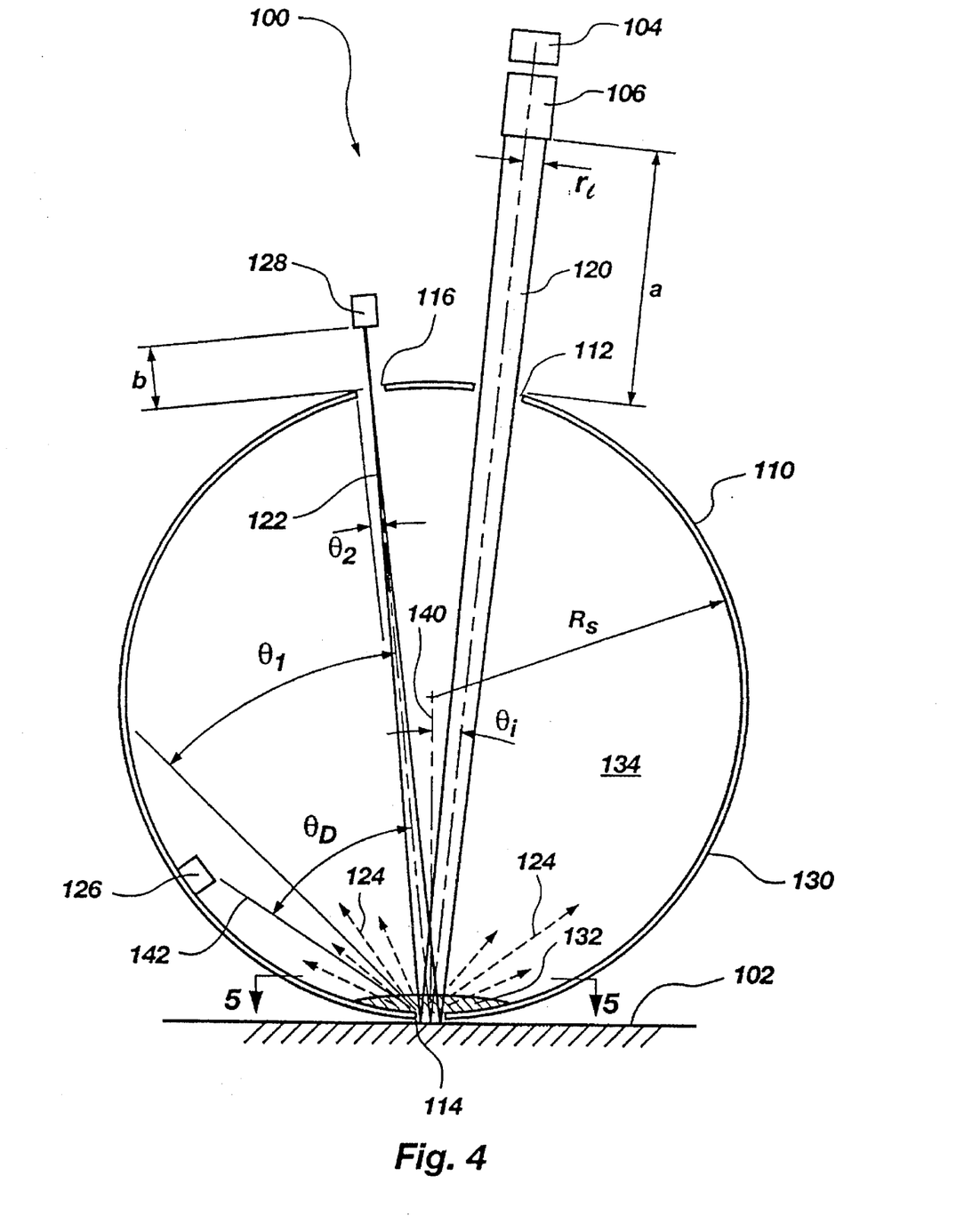
FIG. 4 is a schematic view of an alternative embodiment of the apparatus of the present invention with the integrating sphere illustrated in cross section.

It should be appreciated that the use of an absorption region in an integrating sphere, as discussed herein, greatly improves the performance of any integrating sphere. One embodiment of a conventional integrating sphere measurement system modified to include an absorption region in accordance with the teachings of this aspect of the present invention is illustrated in FIG. 4. In this embodiment, a system 100 for measuring the total integrated scatter of a surface 102 includes a light source 104 capable of producing a beam of light at a known wavelength range. Preferably the light source is a laser source producing light at a known wavelength ($\lambda$). In one presently preferred embodiment, the light source is a laser diode producing a laser beam having a wavelength of 0.670 microns. Of course, the light source 104 may include any of those light sources known for use in an integrating sphere measurement system. Conventional source optics 106 are provided for directing the beam of light generated by the source 104.

The system 100 further includes a hollow sphere 110 having a radius ($R_s$). A radius ($R_s$) of about one to about three inches would be typical. As is standard in integrating sphere measurement systems, the sphere 110 is configured with an input aperture 112, a sampling aperture 114, and an output aperture 116. Each of the apertures is configured with a circular perimeter. The light source 104, source optics 106, and sphere 110 are positioned relative to each other such that an incident beam 120 may be directed through the input aperture 112, through the sampling aperture 114, and onto the surface 102 and such that a specular beam 122 is reflected off the surface and is directed out of the sphere through the output aperture 116. Scattered light 124 reflected off the surface will enter the sphere 110 through the sampling aperture 114 and be retained within the sphere.

A detector 126 is positioned within the sphere 110 to detect the intensity of scattered light 124 within the sphere. A specular detector 128 is positioned outside the sphere for detecting the intensity of the reflected specular beam 122. The specular detector 128 is preferably a "low scatter" detector, thereby reducing the generation of stray light. Detectors 126, 128 may include any of those detectors known for use with such systems; presently preferred detectors include commercially available silicon photo diodes.

As with the integrating sphere 30 of FIG. 3, the integrating sphere 110 in the measurement system of FIG. 4 has an interior surface 130 which includes an absorption region 132 surrounding the sampling aperture 114 with the remainder of the interior surface 130 comprising a reflective region 134. The reflective region 134 is configured to reflect light at the wavelength of the light source and may be made of any of those reflective materials known to those of skill in the art of integrating spheres. One such material is that sold under the SPECTRALON trade name by Labsphere, Inc. of New Hampshire, U.S.A. One presently preferred coating for use in forming the absorption region 132 is black glass.

Importantly, the interior surface 130 is prepared such that the reflectance of the absorption region 132 is less than the reflectance of the reflective region 134 at the wavelength ($\lambda$) of the light source. The reflectance of the absorption region 132 will generally be less than about 10 percent with the reflectance of the reflective region 134 being greater than about 90 percent. It is preferred, however, that the reflectance of the absorption region 132 be less than about 5 percent and the reflectance of the reflective region 134 be greater than, about 95 percent. In this presently preferred embodiment, the absorption region 132 has a reflectance of about 2 percent and the reflective region 134 has a reflectance of about 99.1 percent.

The source optics 106 are preferably configured to focus the specular beam 122 at the output aperture 116 of the hollow sphere. The source optics are additionally configured such that the incident beam 120 has a circular cross section with a radius ($r_1$) as it leaves the source optics.

With the specular beam 122 focused at the output aperture 116, the radius ($r_i$) of the input aperture 112 is preferably sized such that the following relationship is satisfied:

$$r_i = K \frac{4R_S}{4R_S + a} r_1$$

for values of $K \geq 1$, where a is the distance along the beam of light 120 from the source optics 106 to the input aperture 112 of the hollow sphere 110. For a laser-based system, K may be assumed to be greater than or equal to $\sqrt{2.5}$.

The absorption region 132 is preferably configured with a circular perimeter and sized with a radius ($r_{bo}$) which satisfies the following relationship:

$$r_{bo} = \left(1 + \frac{2R_S}{a}\right) r_i + \frac{2R_S}{a} r_1.$$

By configuring the system 100 such that the incident angle ($\theta_i$) of the beam of light 120 is less than about 10 degrees, the radius of the output aperture ($r_0$) may be configured to be approximately equal to $f_{min} 2R_s \lambda$, where $f_{min}$ is the minimum spatial frequency of the total integrated scatter measurement of the surface. Additionally, the radius ($r_s$) of the sampling aperture 114 is determined such that it satisfies the following relationship:

$$r_s = \frac{r_0 - Xr_1}{1 + X},$$

where $$X = \frac{2R_S}{2R_S + a}.$$

Finally, in this embodiment of the present invention, the use of a baffle to shield the scatter detector may be avoided by positioning the scatter detector 126 within the integrating sphere such that the angle ($\theta_D$) between the specular beam 122 and the line 142 between the sampling aperture 114 and the scatter detector 126 is greater than $\theta_{max}$, where $\theta_{max}$ equals $\tan^{-1}(r_s/h)$, where h is the distance from the surface 102 to the interior surface of the hollow sphere at the sampling aperture 114 along the line 140 normal to the surface (compare FIG. 3).

In operation, the system 100 is positioned a predetermined distance from a surface 102 to be inspected. The light source 104 is activated to direct a beam of light into the source optics 106. At the source optics 106, the incident beam 120 is directed through the input aperture 112 and into the sphere 110. The incident beam exits the sphere at the sampling aperture 114 and reflects off the surface 102 creating the, specular beam 122 and scattered light 124. The specular beam 122 passes through the sampling aperture 114, through the output aperture 116, and into the specular detector 128 which measures its power. The scattered light 124 remains within the sphere 110 and is measured by the scatter detector 126.

The total integrated scatter (TIS) of the surface can then be determined by dividing the power of the specular beam 122, as measured by the specular detector 128, into the power of the scattered light 124, as measured by the scatter detector 126. The RMS roughness of the surface 102 can then be determined according to methods well known to one of ordinary skill in the art.

As the light passes through the source optics 106, stray light is generated. In conventional integrating sphere measurement systems, much of the stray light which is introduced into the sphere is measured by the scatter detector, thereby causing errors in the TIS measurement. Such stray light results in what is generally referred to as "optical noise" in the measurements generated by the scatter detector. Hence, any reduction of the optical noise floor will improve the efficiency of the system.

Most stray light is generated by the source optics. The source optics behave as a scatter source of stray light with a spot size equal to the diameter of the incident beam at the lens. The stray light emanates from the source optics in all directions.

Figure 5:
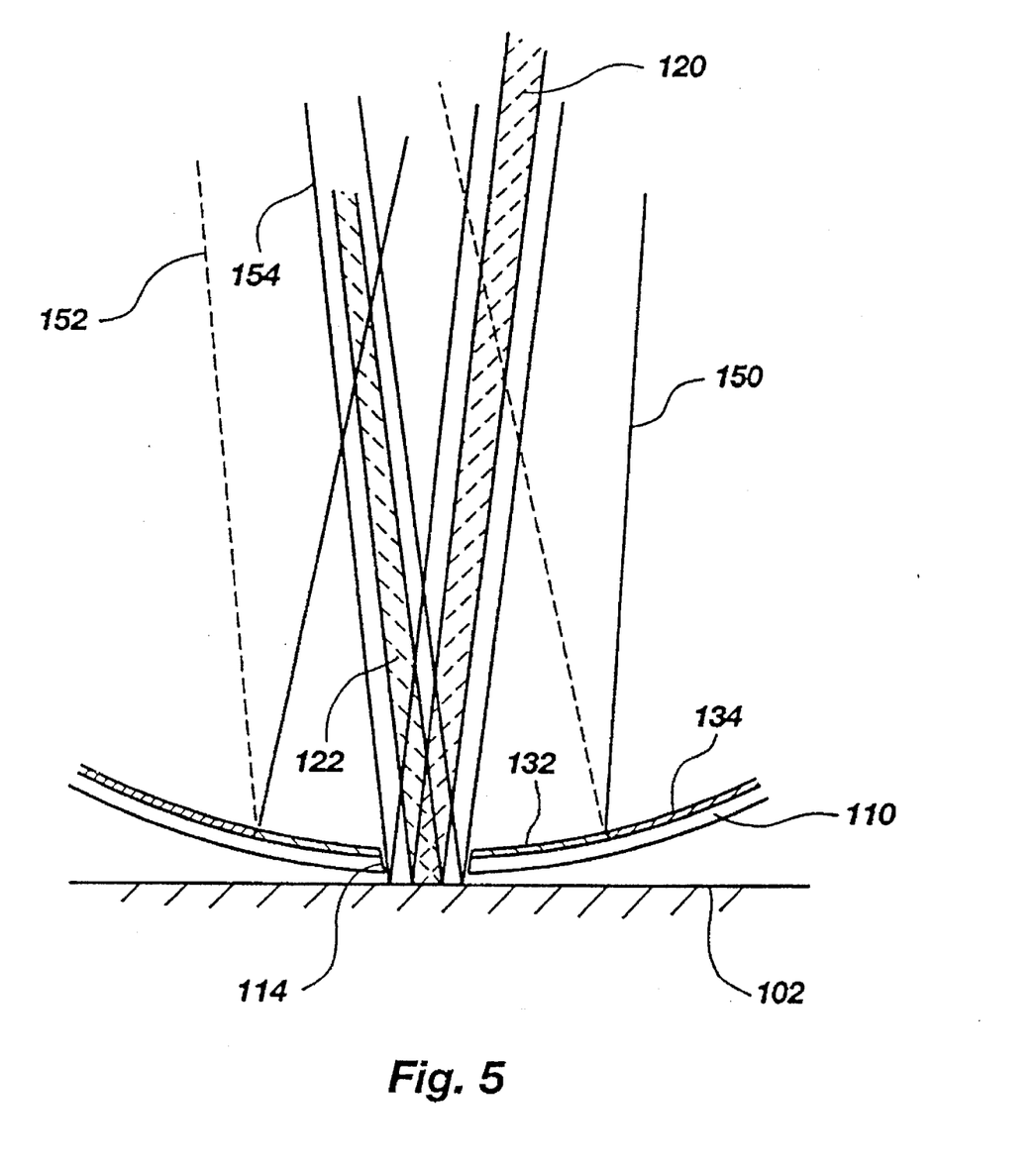
FIG. 5 is a cross-sectional view taken along line of FIG. 4.

By utilizing the present invention, the effect of stray light is substantially eliminated. As illustrated in FIG. 5, the size of the incident stray light cone 150 at the sampling aperture 114 is approximately the same size as the absorption region 132. Thus, when the stray light hits the interior surface 130 of the sphere, instead of reflecting into the sphere, it is absorbed by the absorption region 132. The present invention enables the reflected stray light cone to be reduced from that illustrated in the phantom lines at 152 to the cone 154 which results from specular reflection off the surface 102.

Advantageously, the stray light cone 154 generated from stray light reflected off the surface all exits the sphere through the output aperture 116. Hence, virtually no stray light enters the scatter detector 126. The ability to eliminate substantially all of the stray light from the integrating sphere results in a substantial increase in the measurement accuracy of the system, enabling roughness measurements down to the one Angstrom level to be achieved.

While a small amount of "secondary" stray light will be present when operating the system, this can substantially reduced by ensuring that all system components outside of the sphere 110 are made of, or coated with, a material which absorbs light at the wavelength of the incident beam 120.

The signals from the detectors are processed in accordance with standard signal processing techniques well known in the art. They are amplified, filtered, and processed by an analog-to-digital converter before being processed by a microprocessor. One of skill in the art will readily appreciate how to process the signals to produce output data in a variety of useful forms.

It should be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for measuring the total integrated scatter of a surface, comprising:

a light source for producing an incident beam of light at a known wavelength range;

source optics for directing the incident beam at an incident angle ($\theta_i$);

a hollow sphere having a radius ($R_s$) and configured with an input aperture, a sampling aperture, and an output aperture, the light source, source optics, and sphere positioned such that the incident beam is directed through the input aperture, through the sampling aperture, and onto the surface and such that the specular beam reflected off the surface is directed out of the sphere through the output aperture, the interior surface of the sphere including an absorption region surrounding the sampling aperture, the interior surface of the sphere outside the absorption region comprising a reflective region, the absorption region having a reflectance less than the reflectance of the reflective region over the wavelength range of the light source;

a scatter detector positioned for detecting the intensity of light within the sphere; and a specular detector positioned for detecting the intensity of the reflected specular beam.

2. A system for measuring the total integrated scatter of a surface as defined in claim 1, wherein the light source produces the beam of light at a known wavelength ($\lambda$).

3. A system for characterizing a surface as defined in claim 2, wherein the incident angle of the beam of light ($\theta_i$) is less than about 10 degrees and wherein the output aperture has a circular perimeter with a radius ($r_o$) approximately equal to $f_{min} 2 R_s \lambda$, where $f_{min}$ is the minimum spatial frequency of the total integrated scatter measurement of the surface.

4. A system for characterizing a surface as defined in claim 3, wherein the source optics are configured such that the incident beam has a circular cross section with a radius ($r_1$) as it leaves the source optics and wherein the sampling aperture a circular perimeter with a radius ($r_s$) which satisfies the following relationship:

$$r_s = \frac{r_o - X r_1}{1 + X},$$

where $$X = \frac{2R_s}{2R_s + a},$$

where a equals the distance along the beam of light from the source optics to the input aperture of the hollow sphere.

5. A system for characterizing a surface as defined in claim 4, wherein the scatter detector is positioned within the integrating sphere such that the angle ($\theta_D$) between the specular beam and the line between the sampling aperture and the specular detector is greater than $\theta_{max}$, where $\theta_{max}$ equals $\tan^{-1}(r_s/h)$, where h is the distance from the surface to the interior surface of the hollow sphere at the sampling aperture along a line normal to the surface.

6. A system for measuring the total integrated scatter of a surface as defined in claim 1, wherein the reflectance of the absorption region is less than about 10 percent and the reflectance of the reflective region is greater than about 90 percent.

7. A system for measuring the total integrated scatter of a surface as defined in claim 6, wherein the reflectance of the absorption region is less than about 5 percent and the reflectance of the reflective region is greater than about 95 percent.

8. A system for measuring the total integrated scatter of a surface as defined in claim 1, wherein the absorption region comprises black glass.

9. A system for measuring the total integrated scatter of a surface as defined in claim 1, wherein the source optics are configured to focus the specular beam at the output aperture of the hollow sphere.

10. A system for measuring the total integrated scatter of a surface as defined in claim 9, wherein the source optics are configured such that the incident beam has a circular cross section with a radius ($r_1$) as it leaves the source optics and wherein the input aperture has a circular perimeter with a radius ($r_i$) which satisfies the following relationship:

$$r_i = K \frac{4R_S}{4R_S + a} r_1,$$

for values of $K \geq 1$, where a equals the distance along the beam of light from the source optics to the input aperture of the hollow sphere.

11. A system for characterizing a surface as defined in claim 10, wherein the light source produces a laser beam and $K \geq \sqrt{2.5}$.

12. A system for measuring the total integrated scatter of a surface as defined in claim 1, wherein the source optics are configured such that the incident beam has a circular cross section with a radius ($r_1$) as it leaves the source optics, the input aperture has a circular perimeter with a radius ($r_i$), and wherein the absorption region has a circular perimeter with a radius ($r_{bo}$) which satisfies the following relationship:

$$r_{bo} = \left(1 + \frac{2R_S}{a}\right) r_i + \frac{2R_S}{a} r_1,$$

where a is the distance along the beam of light from the source optics to the input aperture of the hollow sphere.

* * * * *